United States Patent
Klink

(10) Patent No.: US 10,927,017 B2
(45) Date of Patent: Feb. 23, 2021

(54) ARRANGEMENT FOR A DEVICE FOR DISINFECTING A FLUID AND DEVICE

(71) Applicant: HYTECON AG, Lucerne (CH)

(72) Inventor: Maximilian Klink, Lucerne (CH)

(73) Assignee: Hytecon AG, Lucerne (CH)

( * ) Notice: Subject to any disclaimer, the term of this patent is extended or adjusted under 35 U.S.C. 154(b) by 0 days.

(21) Appl. No.: 16/592,540

(22) Filed: Oct. 3, 2019

(65) Prior Publication Data
US 2020/0109066 A1 Apr. 9, 2020

(30) Foreign Application Priority Data

Oct. 4, 2018 (DE) .................... 102018124504.1

(51) Int. Cl.
*A61L 2/10* (2006.01)
*C02F 1/32* (2006.01)

(52) U.S. Cl.
CPC .............. *C02F 1/325* (2013.01); *A61L 2/10* (2013.01); *A61L 2202/122* (2013.01); *C02F 2201/3222* (2013.01); *C02F 2303/04* (2013.01)

(58) Field of Classification Search
CPC .............. C02F 1/325; C02F 2201/3222; C02F 2303/04; C02F 1/32; C02F 2301/026; C02F 2203/006; A61L 2/10; A61L 9/20; A61L 2202/122; A61L 9/12
USPC ................ 250/435, 438, 504 R; 422/159, 24
See application file for complete search history.

(56) References Cited

U.S. PATENT DOCUMENTS

| | | | | |
|---|---|---|---|---|
| 9,303,841 B2 * | 4/2016 | Matsui | .................... | F21V 3/04 |
| 9,533,896 B2 | 1/2017 | Lee et al. | | |
| 10,266,426 B1 * | 4/2019 | Conrad | .................... | A61L 2/10 |
| 10,377,644 B2 * | 8/2019 | Kolch | ...................... | C02F 1/42 |
| 10,604,423 B2 * | 3/2020 | McNulty | .................. | C02F 1/76 |
| 2007/0053188 A1 * | 3/2007 | New | ........................ | B60Q 3/47 |
| | | | | 362/276 |
| 2009/0012459 A1 * | 1/2009 | Sobue | .................. | A61M 39/18 |
| | | | | 604/29 |
| 2010/0237254 A1 * | 9/2010 | Mason | ...................... | A61L 9/20 |
| | | | | 250/435 |
| 2012/0318749 A1 * | 12/2012 | Stokes | .............. | G01N 21/5907 |
| | | | | 210/748.09 |

(Continued)

FOREIGN PATENT DOCUMENTS

| EP | 2567713 A1 | 3/2013 |
|---|---|---|
| EP | 3323433 A1 | 5/2018 |

(Continued)

*Primary Examiner* — David A Vanore
(74) *Attorney, Agent, or Firm* — Harness Dickey

(57) ABSTRACT

The invention relates to an arrangement for a device for disinfecting a fluid, having a container; a reactor space which is arranged in the container and is configured to receive a fluid to be disinfected, which enters the reactor space via an inlet thereof and can leave it via an outlet of the reactor space; and a UV irradiation device having light-emitting UV diodes, with which UV light rays for disinfecting the fluid in the reactor space can be irradiated; wherein the reactor space in the container is formed having a flow path in a flow tube surrounded by a container wall and the light-emitting UV diodes are arranged distributed on the container wall in the region of the flow tube along the flow path in order to irradiate the UV light rays on the flow path. Furthermore, a device for disinfecting a fluid is provided.

10 Claims, 1 Drawing Sheet

(56) References Cited

U.S. PATENT DOCUMENTS

Figure 1:
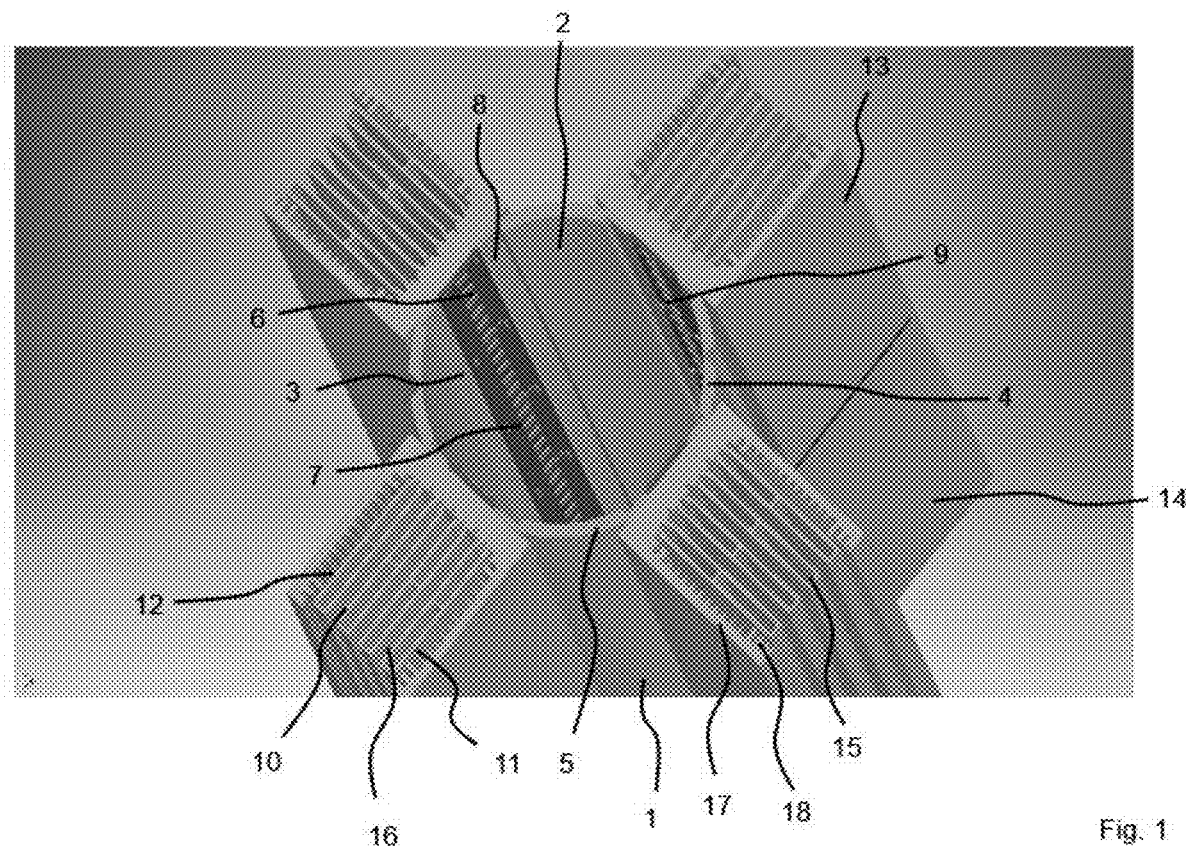

| | | | | |
|---|---|---|---|---|
| 2014/0163664 A1* | 6/2014 | Goldsmith | ....... | A61B 17/12181 |
| | | | | 623/1.11 |
| 2014/0322073 A1* | 10/2014 | Link | ...................... | B66B 31/02 |
| | | | | 422/24 |
| 2015/0060693 A1* | 3/2015 | Lee | ......................... | C02F 1/325 |
| | | | | 250/435 |
| 2015/0284266 A1* | 10/2015 | Matsui | .................... | C02F 1/325 |
| | | | | 422/24 |
| 2016/0003791 A1* | 1/2016 | Lebedev | ................ | G01N 33/15 |
| | | | | 422/82.05 |
| 2016/0136312 A1* | 5/2016 | Park | .................... | F21V 33/0044 |
| | | | | 362/231 |
| 2016/0168384 A1* | 6/2016 | Guidolin | ................. | A61L 2/084 |
| | | | | 250/436 |
| 2017/0005235 A1* | 1/2017 | Chou | ................... | H01L 51/5281 |
| 2017/0130952 A1* | 5/2017 | Xu | .......................... | F21V 23/06 |
| 2018/0093907 A1* | 4/2018 | Kaddoura | ............ | C02F 3/1242 |
| 2018/0257953 A1* | 9/2018 | Mochizuki | ................ | A61L 2/26 |
| 2019/0184045 A1* | 6/2019 | Mochizuki | ............. | B01J 19/123 |
| 2019/0321505 A1* | 10/2019 | Kodama | ................... | A61L 9/20 |
| 2020/0109066 A1* | 4/2020 | Klink | ........................ | A61L 2/10 |

FOREIGN PATENT DOCUMENTS

| | | | | |
|---|---|---|---|---|
| KR | 20160080791 A | 7/2016 | | |
| WO | WO-2006063212 A2 | 6/2006 | | |
| WO | WO-2013086274 A1 * | 6/2013 | ............. | C02F 1/325 |
| WO | WO-2014143882 A1 | 9/2014 | | |
| WO | WO-201608807 A1 | 1/2016 | | |
| WO | WO-2017045662 A1 | 3/2017 | | |

\* cited by examiner

ARRANGEMENT FOR A DEVICE FOR DISINFECTING A FLUID AND DEVICE

CROSS REFERENCE TO RELATED APPLICATIONS

This application claims the benefit and priority of DE102018124504.1, filed Oct. 4, 2018. The entire disclosure of the above application is incorporated herein by reference.

FIELD

The invention relates to an arrangement for a device for disinfecting a fluid and a device.

BACKGROUND

The disinfection of fluids, for example, water or drinking water, is provided in connection with a variety of applications. A contaminated or unsuitable fluid is disinfected in order to then be provided in disinfected form for a further use. For example, water is disinfected in this way in order to provide it, for example, as drinking water, in particular at a point of use.

Document WO 2018/050144 A1 discloses a decentralized water disinfection device. UV light rays from UV light-emitting diodes are used to disinfect the water in a reactor space. Document DE 10 2016 122 075 A1 discloses a working method and a device for monitoring a UV disinfection system. UV light rays are used to disinfect a fluid in a reactor space.

SUMMARY

The object of the invention is to provide an arrangement for a device for disinfecting a fluid and a device for disinfecting a fluid, with which an improved disinfection of the fluid can be achieved.

As a solution, an arrangement for a device for disinfecting a fluid. Further, a device for disinfecting a fluid. Embodiments are the subject of dependent claims.

According to one aspect, an arrangement for a device for disinfecting a fluid is provided, said device having a container and a reactor space arranged in the container. The reactor space is configured to receive a fluid to be disinfected, which can reach the reactor space via an inlet of the reactor space and can leave it via an outlet of the reactor space. Furthermore, a UV irradiation device is provided which has light-emitting UV diodes, with which UV light rays can be irradiated into the reactor space for disinfecting the fluid. The reactor space is formed in the container with a flow path in a flow tube surrounded by a container wall. The light-emitting UV diodes are arranged distributed on the container wall in the region of the flow tube along the flow path in order to irradiate the UV light rays on the flow path.

Furthermore, a device for disinfecting a fluid is provided with such an arrangement.

A reactor can be provided for a device for disinfecting a fluid with the arrangement, for example, for disinfecting water, in particular drinking water. The reactor can also be referred to as a tube reactor because of the formation of the reactor space with the flow path in the flow tube.

The arrangement of the light-emitting UV diodes can extend over the entire length of the flow path along the container wall.

The inlet of the reactor space and/or the outlet of the reactor space can be formed in the region of end sections of the flow tube.

The container can be designed in modular construction, such that the flow tube is composed of container modules in which at least one light-emitting UV diode is arranged on a module body with a aperture, which UV diode irradiates during operation in the aperture, and the apertures of the composite container modules together form the flow tube with the flow path. In this embodiment, the container modules can be assembled with the aid of connecting elements, for example, by means of a plug connection, to then provide the flow path in the flow tube by means of the apertures of the container modules. The modular design makes it possible to flexibly provide flow tubes of different lengths for different application situations. The module body can be designed in one piece, for example, as an injection-molded component.

In one example, flow-conducting elements can be arranged on the inner surface of the container wall in the region of the flow tube in order to guide or conduct the fluid to be disinfected when flowing or flowing through the flow tube, for example, for inducing vortices, which can improve the irradiation with the UV light. Also, a spiral-shaped flow of the fluid in the flow tube can be selectively induced with the aid of the flow-conducting elements.

At least a part of the light-emitting UV diodes can be arranged to form at least one line arrangement of diodes on the container wall. The light-emitting UV diodes can be arranged at equal or different distances between adjacent diodes along the line arrangement of diodes or line-shaped diode arrangement. A chain of UV radiation sources can be formed by means of the UV diodes along the line arrangement of diodes. The line arrangement of diodes can have one or more sections of the following type: straight line, zigzag line, spiral line and wavy line. One or more of the line arrangements of diodes can extend substantially parallel to the passage direction of the flow tube. If the container wall has flow-conducting elements on the inside, one or more line arrangements of diodes can run along the flow-conducting elements, for example, parallel thereto. Alternatively or in addition to the line arrangements of diodes, light-emitting UV diodes can be arranged individually or in groups in the region of the container wall at the flow path.

The line arrangement of diodes can extend along a slot recess of the container wall. In this or other embodiments, the light-emitting UV diodes can be embedded in an associated aperture of the container wall, wherein the light-emitting UV diodes are sealed in the aperture so that the flow path is sealed fluid-tight against the environment of the container. It can be provided that the light-emitting UV diodes are arranged behind a transparent window for the UV light rays, which window is sealed integrated into the container wall.

In the various embodiments, a radiation region of the light-emitting UV diodes, in which the UV light generated by the diode is radiated, is aligned with the flow path for the fluid to be disinfected.

The light-emitting UV diodes can be arranged distributed on the container wall in the region of the flow tube around the flow path. A plurality of line arrangements of diodes can be formed around the flow path, for example, a plurality of straight line arrangements of diodes extending in the passage direction of the flow tube. A paired line arrangement of diodes opposite one another can be provided.

The light-emitting UV diodes can each be associated with a cooling device arranged outside the reactor space, which is configured to cool the light-emitting UV diodes during operation. The cooling device serves to dissipate heat energy generated by the light-emitting UV diode during operation, in order to promote safe operation of the light-emitting UV diodes. An active cooling, in which the heat energy is dissipated by means of a coolant, and/or a passive cooling can be provided, which is free of coolant and, for example, has heat sinks.

The cooling device can have cooling elements extending away from the container. The cooling elements can, for example, have cooling fins extending away from the container so as to dissipate the heat energy generated during operation. Cooling fins can be designed with internal cavities or chambers which are formed free of a flow of cooling fluid or alternatively through which a cooling medium flows. Elongated cooling fins with respectively one or more internal cavities, in particular two in cross-section substantially identically formed cavities or chambers can be adjacent and spaced from one another, for example, as cooling fins extending straight (radially) from the reactor space. Non-closed (radially outwardly open) intermediate spaces can be arranged between the cooling fins, which, for example, can have a substantially same width as the cooling fins with internal cavities. Such cooling fins can be arranged between external cooling fins on both sides, which in one embodiment have an internal arrangement of cooling fin projections, which run transversely to the longitudinal direction of the cooling fins having internal cavities and project towards them. The arrangement of the cooling fins can be removably mounted.

Active cooling elements can also be designed to extend away from the container.

The cooling device can have a coolant passage through which the coolant can flow through during operation for cooling in order to provide active cooling, for example, in the cavities of the cooling fins. The coolant passage can comprise channels and/or cavities to receive a coolant during operation which serves to dissipate the heat energy generated by the light-emitting UV diodes. In this case, a closed coolant circuit can be provided, in which coolant is supplied from a coolant reservoir into the coolant passages and then discharged therefrom back to the reservoir.

Cooling devices can be formed as a common cooling device for at least two of the light-emitting UV diodes. For example, UV light-emitting diodes arranged adjacent to one another can have a common cooling device, for example, in the line arrangement of diodes. In this case, a single cooling device can be provided per line arrangement of diodes for all light-emitting UV diodes comprised hereof. The common cooling device can comprise common cooling fins or bodies and/or common coolant passages for the light-emitting UV diodes.

At least in sections, the container wall can be made of a material that diffusely reflects the UV light rays, at least on the surface side. The formation of the container wall on the surface side material diffusely reflecting from the UV light rays can be provided by means of a solid material section of the container wall or by means of a surface-side coating on the container wall.

The container wall can in particular be between the line arrangements of diodes, at least on the surface side, in sections, or completely made of the material that diffusely reflects the UV light rays.

It can be provided that a section of the container wall is arranged opposite the light-emitting UV diodes, which is at least in sections or completely made of material diffusely reflecting UV light rays on the surface side, so that the light emitted by the light-emitting UV diodes is incident on this section, which can be completely free of UV diodes, and diffusely reflected.

In the case of the coating, said coating can have a minimum thickness of about one millimeter in order to reduce losses of UV light rays in the region of the surface. At least on the surface side, the reactor space can be completely made of the material diffusely reflecting the UV light rays in the region of the flow path. For example, quartz or polytetrafluoroethylene can be used in the various embodiments as material for the container wall. Polytetrafluoroethylene can also be used to provide a surface coating.

This ensures that the light rays irradiated for disinfecting the fluid are reflected to the greatest possible extent from the layer and reflected into the fluid to be disinfected, for example, water, so as to optionally contribute more to disinfecting. It has been found that a loss of the light rays due to transmission through the surface is largely avoided with the provided layer thickness of at least 1 mm for the coating or the solid material.

The coating of the container wall can be back injected with a plastic material. The coating and the layer of plastic material produced by means of back injection, for example, a polymer material, can have a substantially identical layer thickness or different layer thicknesses in the layer composite of the container wall. It can be provided that the coating has a smaller layer thickness than the plastic layer. An outer container wall can be formed with the back-injected plastic material. The layer produced by means of back injection of the plastic material here forms the outer layer of the container wall. Further layers can optionally be provided for the construction of the container wall.

In one embodiment, the material diffusely reflecting the UV light rays is configured to diffusely reflect UV light in a range from about 200 nm to about 300 nm.

The material diffusely reflecting the UV light rays can have a reflectance of at least about 90% for the UV light rays. Alternatively, a reflectance of at least about 95% or at least about 98% can be formed. In one embodiment, the reflectance for the UV light rays is at most about 98%.

The material diffusely reflecting the UV light rays is UV resistant. The UV resistance can in particular mean that the material diffusely reflecting UV light rays does not discolor and/or does not embrittle due to irradiation with UV light. The material diffusely reflecting UV light rays can be thermally stable up to temperatures of about 200° C. In one embodiment, it can be provided that the inner layer is thermally stable up to a temperature of about 260° C.

In particular, a disinfection of water or drinking water can be provided in order to process water to drinking water or to improve the water quality for existing drinking water by means of disinfection.

It can be provided that a filter device is arranged upstream of the reactor space, in which filter device the fluid to be disinfected is filtered prior to introduction into the reactor space, for example, using an activated carbon filter. The filter device can be designed as part of the disinfection device or be upstream thereof.

The embodiments explained above in connection with the arrangement apply correspondingly in conjunction with the device for disinfecting the fluid.

DETAILED DESCRIPTION

Figure 2:
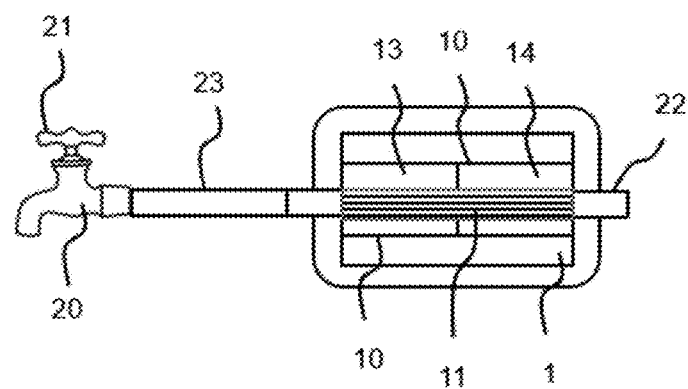

Further embodiments are explained in more detail with reference to figures of a drawing in the following. Shown thereby:

FIG. 1 a schematic perspective representation of an arrangement for a device for disinfecting a fluid by means of UV light and FIG. 2 a schematic representation of a device for disinfecting a fluid.

FIG. 1 shows a schematic perspective representation of an arrangement for a device for disinfecting a fluid. The arrangement has a container 1, in which is formed a reactor space 2 having a flow path 3 along a flow tube 4. The reactor space 2 serves, during operation of a device for disinfecting a fluid, to receive the fluid to be disinfected and to irradiate it with UV light rays for disinfecting. For this purpose, light-emitting UV diodes 6 are arranged along the flow path 3 on a container wall 5. In the example shown, the light-emitting UV diodes 6 are arranged in line arrangements of diodes 7, which extend continuously along the flow path 3. The line arrangements of diodes 7 are each arranged in an associated recess 8 of the container wall 5, such that the flow path 3 is sealed fluid-tight against the environment.

A UV irradiation device 9 is formed with the light-emitting UV diodes 6. In this, a cooling device 10 is in each case associated with the line arrangements of diodes 7, which in the illustrated embodiment is formed with a heat sink 11, which has cooling fins 12, wherein the cooling fins 12, like the entire heat sink 11, extend away from the container 1. Alternatively or additionally, the cooling devices 10 can have coolant passages in order to allow a coolant to flow through them during operation, so that heat energy generated by the light-emitting UV diodes 6 during operation is dissipated.

In the embodiment shown in FIG. 1, the light-emitting UV diodes 6 are arranged circumferentially around the flow path 3, in particular in a paired line arrangement of diodes opposite one another. Other embodiments for the arrangement of the light-emitting UV diodes 6 around the flow path 3 can be provided.

In the embodiment in FIG. 1, the container 1 is formed from a first and a second container module 13, 14, such that passages of the first and second container module 13, 14 together form the flow tube 4 with the flow path 3. The connection between the first and the second container module 13, 14 can be detachable or non-detachable. This modular design allows the production of containers having different sized container spaces, each extending along the flow tube 4.

The cooling fins 11 are designed with internal cavities or chambers 15, which are formed free of a cooling fluid flow or alternatively have cooling medium flow therethrough. Elongated cooling fins 11 having one or more respective internal cavities, in particular two substantially identically formed cavities or chambers that are equal in cross section, are arranged adjacent and spaced from one another, in the embodiment as from the cooling fins extending straight (radially) from the reactor space 2. Non-closed (radially outwardly open) intermediate spaces 16 are arranged between adjacent cooling fins 11, which intermediate spaces can have, for example, a substantially same width as the cooling fins 11 having internal cavities. The cooling fins 11 are arranged between external cooling fins 17 on both sides, which have, in the embodiment shown, an internal arrangement of cooling fin projections 18 which run transversely to the longitudinal direction of the cooling fins 11 with the internal cavities 15 and project towards them.

FIG. 2 shows a schematic representation of a device for disinfecting and discharging a fluid, in particular water, for example, drinking water, having the arrangement of FIG. 1. The disinfected fluid is dispensed at a point of use 20, which is equipped, for example, with a water tap 21. The fluid to be dispensed and to be disinfected is supplied via a supply connection 22 in order to reach the container 1 for disinfecting. The outlet of the container 1 couples to a discharge port 23, which leads to the point of use 20.

The features disclosed in the above description, the claims, and the drawings can be important both individually and in any combination for the realization of the various embodiments.

What is claimed is:

1. Arrangement for a device for disinfecting a fluid, having
a container;
a reactor space which is arranged in the container and configured to receive a fluid to be disinfected, wherein the fluid can reach the reactor space via an inlet of the reactor space and can leave the reactor space via an outlet of the reactor space; and
a UV irradiation device which has light-emitting UV diodes, with which UV light rays can be irradiated into the reactor space for disinfecting the fluid;
wherein the reactor space is formed in the container with a flow path in a flow tube surrounded by a container wall, and the light-emitting UV diodes are arranged distributed on the container wall in the region of the flow tube along the flow path in order to irradiate the UV light rays on the flow path, wherein the light-emitting UV diodes include a first light-emitting UV diode associated with a first cooling device and configured to cool the first light-emitting UV diode during operation, and a second light-emitting UV diode associated with a second cooling device and configured to cool the second light-emitting UV diode during operation, wherein the cooling devices are arranged outside the reactor space.

2. The arrangement according to claim 1, includes at least a part of the light-emitting UV diodes is arranged to form at least one line arrangement of diodes on the container wall.

3. The arrangement according to claim 2, includes the line arrangement of diodes extends along a slot recess of the container wall.

4. The arrangement according to claim 1, includes the light-emitting UV diodes on the container wall are arranged distributed in the region of the flow tube around the flow path.

5. The arrangement according to claim 1, includes a cooling device arranged outside the reactor space is associated with each of the light-emitting UV diodes, which cooling device is configured to cool the light-emitting UV diodes during operation.

6. The arrangement according to claim 5, includes the cooling device has cooling elements extending away from the container.

7. The arrangement according to claim 5, includes the cooling device has a coolant passage, through which a coolant can flow through for cooling during operation.

8. The arrangement according to claim 5, includes cooling devices are formed for at least two of the light-emitting UV diodes as a common cooling device.

9. The arrangement according to claim 1, includes the container wall is made of a material diffusely reflecting the UV light rays at least on the surface side at least in sections.

10. The arrangement according to claim 1, wherein the container is configured, such that the flow tube is composed of container modules in which at least one light-emitting UV diode is arranged on a module body with an aperture, which UV diode irradiates in the aperture during operation, and the apertures of the composite container modules together form the flow tube having the flow path.

* * * * *